United States Patent [19]

Scheinberg

[11] Patent Number: 4,676,233
[45] Date of Patent: Jun. 30, 1987

[54] MANUALLY FORMED SPLINTS HAVING SHEET METAL STRUCTURE

[76] Inventor: Samuel Scheinberg, 2930 W. Devil's Lake Rd., Lincoln City, Oreg. 97367

[21] Appl. No.: 700,632

[22] Filed: Feb. 12, 1985

[51] Int. Cl.⁴ .............................................. A61F 5/04
[52] U.S. Cl. ................................ 128/87 R; 128/87 B; 128/89 R; 128/DIG. 23
[58] Field of Search ...................... 128/85, 87 A, 87 B, 128/87 C, 87 R, 89 R, 90, DIG. 23; 229/DIG. 1; 206/586, 593

[56] References Cited

U.S. PATENT DOCUMENTS

| | | | |
|---|---|---|---|
| 2,818,063 | 12/1957 | Smith et al. | 128/87 B |
| 2,934,251 | 4/1960 | Kramer | 206/586 |
| 3,089,486 | 5/1963 | Pike | 128/90 |
| 3,943,923 | 3/1976 | Scheinberg | 128/89 R |
| 4,161,175 | 7/1979 | Bentele | 128/89 R X |
| 4,538,597 | 9/1985 | Lerman | 128/87 B X |

Primary Examiner—Robert A. Hafer
Assistant Examiner—Kathleen J. D'Arrigo
Attorney, Agent, or Firm—Chernoff, Vilhauer, McClung & Stenzel

[57] ABSTRACT

Splints for immobilizing and supporting injured limbs, fingers, or the neck of a patient may be fashioned of thin malleable sheet metal, preferably dead soft aluminum, provided in the form of a flat strip folded to a convenient, compact shape for storage. For use as a splint, the aluminum sheet is bent to include a stiffening flange or rib extending longitudinally and centrally along the material to support the body member on which the splint is used. The same material may be formed as a cervical collar including a plurality of vertically-extending, outwardly-projecting stiffening flanges. The sheet metal is preferably covered by a layer of adhesively attached, resilient plastic foam material which insulates, cushions, and helps to prevent the splint from shifting relative to the body of the person on which it is used.

19 Claims, 11 Drawing Figures

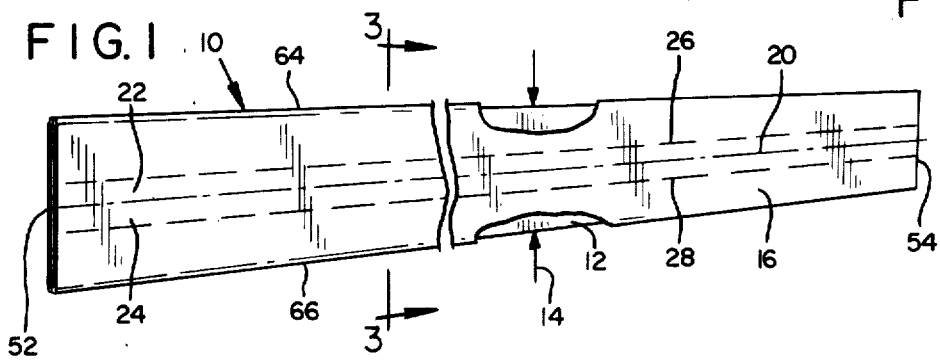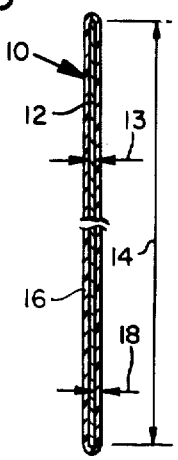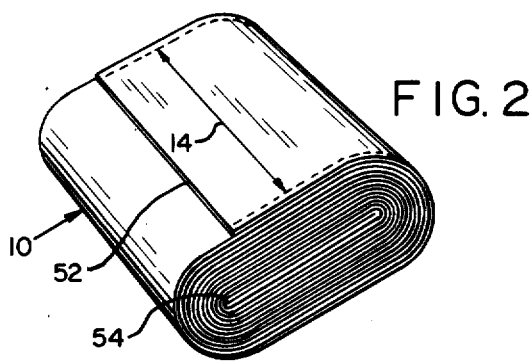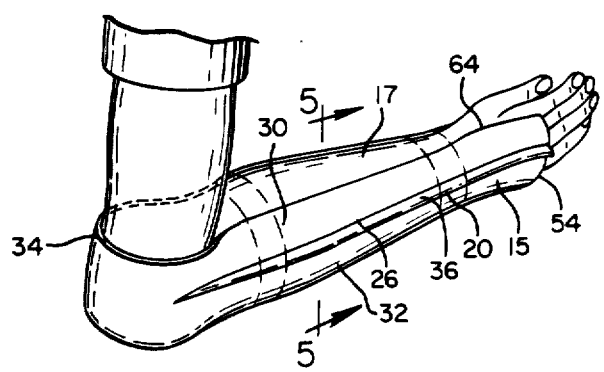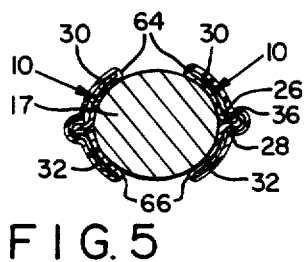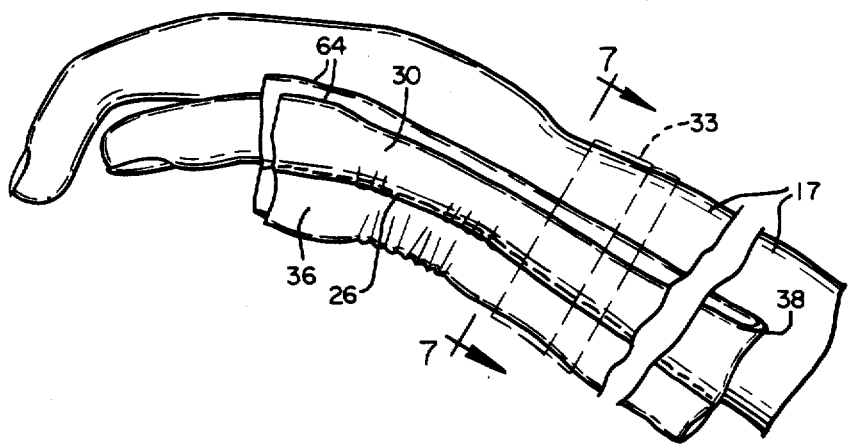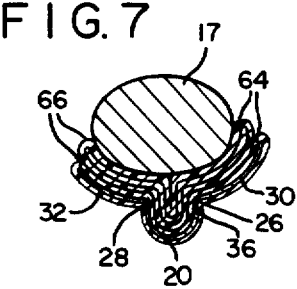

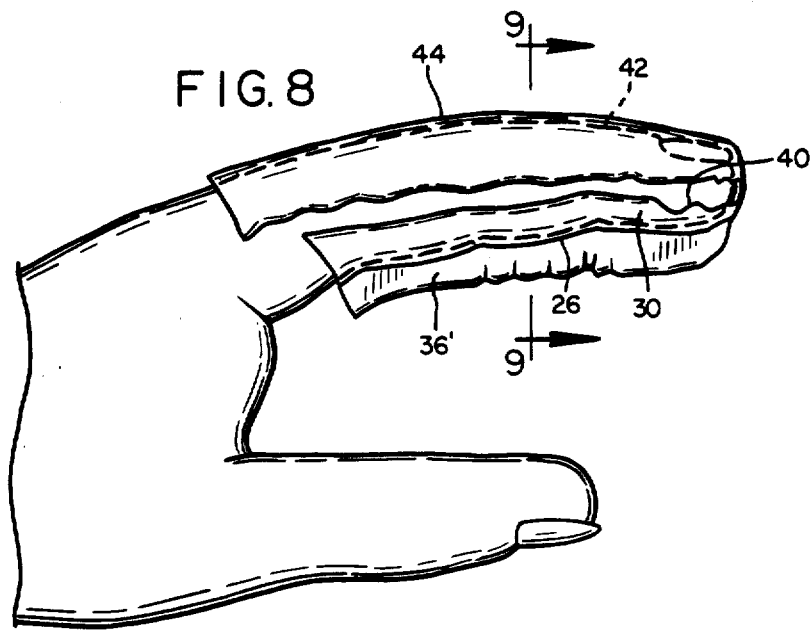
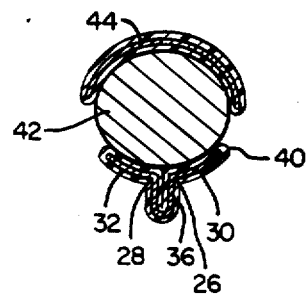
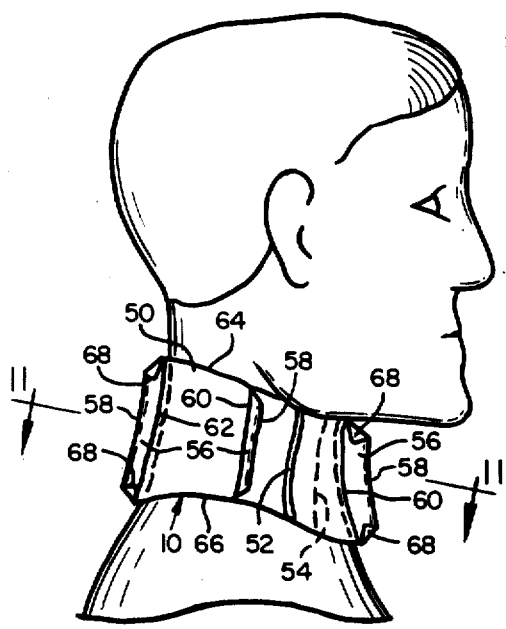
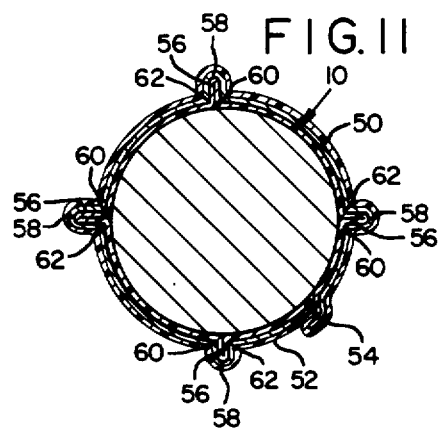

MANUALLY FORMED SPLINTS HAVING SHEET METAL STRUCTURE

BACKGROUND OF THE INVENTION

The present invention relates to splints for use in immobilizing injured body members, and particularly to an improved splint of sheet metal construction.

In moving injured people from an accident site to a location where bone fractures and dislocations can be reduced and cast, it is important for minimization of further trauma that injured members be immobilized as well as possible by the proper use of splints. While a serviceable splint can be fashioned from nearly any stiff material, many previously known splints designed for use by medical emergency personnel at the site of, e.g., an automobile accident, have serious shortcomings.

For example, inflatable plastic splints, which derive their ability to provide support from the shape of individual inflated air cells, often exert an undesired amount of pressure upon portions of an injured limb which is desired to be immobilized. Such splints, are also susceptible to being punctured, particularly at the scene of an automobile accident, where shards of glass may be present and may even be embedded in the clothing or skin of an accident victim. Inflatable splints are, to some extent, self-molding to accommodate the shape of the victim. In general, however, they must be provided in a variety of different sizes to well accommodate all the possibilities. A further problem of inflatable splints is that they are likely to be uncomfortably hot, tending to cause perspiration which might result in additional contamination of skin wounds.

Splints are easily made of cardboard or corrugated paper board, but they do not stand up well where they are subjected to moisture, as where a person is injured while outdoors in bad weather conditions or where a wound continues to discharge fluid. Such cardboard splints need to be padded to prevent uncomfortable pressure and also to prevent chafing.

Casting tape, containing a plaster which quickly reacts with water to harden, may be difficult or impossible to use at an accident scene, and forms a cast which is opaque to X-rays.

Preshaped metal splints, of stamped or forged sheet aluminum, for example, are available, but do not fit precisely in many cases, because of the different sizes of patients and the variation from normal configuration when bones have been broken. While such splints may, to some extent, be bent to fit a patient, such bending is difficult to accomplish and ordinarily would require the use of tools. Because of the rigidity of such splints, padding is necessary for their use.

A common disadvantage of all of the types of splint materials mentioned above is that they require a considerable amount of room for storage and thus can usually not be carried in an emergency vehicle or emergency medical pack in all of the sizes which might be needed. Compromises must be made often, therefore, in using a splint made of such materials.

Scheinberg U.S. Pat. No. 3,943,923 discloses a splint made of an elongate sheet of PVC coated malleable aluminum, thin enough to be bent by hand, with the sheet bent into the form of generally round-bottomed U-shaped elongate splint members extending longitudinally along the opposite sides of an injured limb as a splint. It is desired, however, to provide a splint which is more precisely conformed to the patient, particularly where bones of a limb have been broken and the limb has been bent into an unusual configuration which is not easily accommodated by a substantially straight splint as provided by the previous Scheinberg invention.

Where neck injuries are involved, a key requirement for safety of a patient is to immobilize the patient's head and neck as completely as possible. This requires that a neck brace or cervical splint be able to conform to the patient and provide ample support for the patient's neck and head. This has not been easily accomplished using previously available splints. While the well-known bulky collars of resilient foam material provide ample support, application of such a collar may be excessively difficult to accomplish without disturbing the location of the patient's neck and head. Because of the possible injury of the spinal cord where a neck injury has occurred, it is desired to have a neck splint which can be applied with a minimum of movement of the patient.

Injured fingers often need to be splinted where the bones or joints have been broken or dislocated, and also in case of surgery performed on the fingers. In the case of surgery, not only is it important to immobilize the fingers, at least temporarily, but it is also desirable to provide protection against accidental bumping. Previously available splints for use in supporting or protecting fingers have been unnecessarily clumsy and difficult to use.

In view of the above, it is desired to provide an improved splint material and a splint made from such material for use in supporting and immobilizing limbs, fingers, and the neck of a patient, and to be able to use a single, compactly packagable material as a splint in any of several of such possible situations. Preferably, such splint material should be able to be stowed in a small space until its use is required, so that it can be easily carried by medical personnel. Additionally, preparation and use of a splint from such splint material should be possible in a short time and without special tools.

SUMMARY OF THE INVENTION

The present invention provides an improved material and methods for its use in preparing splints which avoid many of the shortcomings of the previously available splints and the previously available splint materials. In accordance with the present invention a thin soft metal sheet, preferably having a protective cushioning covering such as a layer of a soft microcellular foam plastic, is provided in a small package, from which it may be opened into a relatively narrow elongate sheet. This sheet may then be bent to include a stiffening longitudinal flange and to conform to a patient's injured body member. The metal sheet, which is otherwise too soft and flexible to support and immobilize a body member, may easily be formed manually into a structural beam configuration having a "T" cross section shape, with the cross bar, or arms, of the "T" lying substantially in supporting contact with the surface of the injured member. The stem, or base, of the "T" extends away from the injured member as a stiffening flange or rib, with a properly oriented double thickness of the sheet of metal thereby providing the required structural rigidity to support the injured member.

Additionally, the material provided by the present invention may be formed into a cervical splint, in the form of a collar, in a configuration including a plurality of ribs or flanges extending longitudinally along the patient's neck at spaced-apart locations about the neck. These flanges provide the required amount of stiffnesa to support the patient's neck and head, while the inherent flexibility of the sheet metal permits it to be bent to a shape conforming closely to the patient. Thus the upper and lower edges of the cervical splint of the invention, formed by wrapping a thin elongate sheet of padded metal around the neck of the patient, can be bent to rest comfortably against the patient's head, jaw, collar bones, chest and back to provide ample support and rigidity for adequate protection of an injured neck.

While capable of providing sufficient support for injured body members, the material used in the present invention is, nevertheless, transparent to X-rays. As a result, radiographic examination is possible without removal of a splint according to the present invention.

It is therefore a principal object of the present invention to provide an improved splint for use by medical emergency personnel for immobilizing fractured limbs and the like.

It is another important object of the present invention to provide an improved cervical collar or neck splint which is easilY fashioned to fit the patient, yet provides needed support and is readily portable in a configuration which occupies a minimum amount of space.

It is an important feature of the present invention that it provides a thin malleable sheet of metal as material for a splint having a configuration resembling a "T" in cross section, which provides sufficient structural rigidity to properly support an injured body member, yet is easily bent by hand to a required form, and can be stored in a configuration occupying a minimum amount of space.

It is another important feature of the present invention that it provides a thin elongate sheet of malleable metal covered with a layer of resilient padding material, and manually bendable into a required shape for use as a splint for supporting the injured limbs or neck of a patient.

It is a principal advantage of the present invention that it provides a material for use in constructing a splint molded to the shape of a deformity to fit a patient better than splints made from previously available materials and yet which provides ample support for injured body members.

It is another important advantage of the present invention that it provides a splint which can be used without separate padding, unlike most previously available splints.

BRIEF DESCRIPTION OF THE DRAWINGS

FIG. 1 is a view showing an elongated strip of material for use according to the present invention in making splints for supporting injured body members.

FIG. 2 shows the splint material of FIG. 1 in a compact form in which it may be packaged for inclusion in medical emergency kits.

FIG. 3 is a sectional view, taken along line 3—3 of FIG. 1, of the splint material of the present invention.

FIG. 4 is a view of the splint material of FIG. 1 in use according to the present invention as a splint for supporting a person's arm.

FIG. 5 is a sectional view, taken along line 5—5, of the splinted arm shown in FIG. 4.

FIG. 6 is a view of a hand and wrist supported by a splint according to the present invention.

FIG. 7 is a sectional view taken along line 7—7 of the wrist splint shown in FIG. 6.

FIG. 8 is a view of a finger splint according to the present invention in use on a patient's hand to support an injured finger.

FIG. 9 is a sectional view taken along line 9—9 of the finger splint shown in FIG. 8.

FIG. 10 is a view of a cervical splint according to the present invention being used to support the neck of a patient.

FIG. 11 is a sectional view taken along line 11—11 showing the configuration of the cervical brace shown in FIG. 10.

DETAILED DESCRIPTION OF THE INVENTION

Referring now to FIGS. 1-5 of the drawings, a piece 10 of splint material according to the present invention, in a preferred embodiment, includes an elongate sheet 12 of malleable metal, preferably a shcet of aluminum. The aluminum is soft and untempered and preferably has a thickness 13 in the range from 0.005 inch to 0.025 inch so that it is easily bendable by hand to a desired shape for use as a splint. The sheet of aluminum preferably has a width 14, for example, of at least 3½ inches for adults, and has a length adequate for use as a splint 15 for an injured limb 17, for example at least 20 inches, and preferably at least 36 inches.

Each generally flat face and the edges of the aluminum sheet 12 are preferably covered by a layer of an X-ray-transparent resilient padding, such as foam material 16, attached to the aluminum sheet 12 by a flexible adhesive. The foam material 16 may be of either the closed-cell or open-cell type, and is provided for the purposes of thermal insulation, padding, a texture intend to provide comfort for the patient, and to some extent to resist slippage of the splint 15 along the skin of the patient.

While the thickness 18 of the foam layer 16 is not critical, a preferred thickness is in the range of ⅛ to ¼ inch. 1/32 inch is considered to be a minimum effective thickness, while a layer as thick as ½ inch may be useful. An acceptable foam material is a microcellular low density closed-cell expanded ethylene vinyl acetate with a flexible adhesive material already applied to one side of the foam, manufactured by Monarch Rubber Co. of Baltimore, MD., and available under the trademark "Bevalite" from Boyd Corporation of Portland, Oreg. Such material is available in roll form and can be applied to the sheet 12 of aluminum as shown in FIGS. 1 and 3, or may be applied in a thickness 18 of ⅛ inch on one side and ¼ inch on the other side of the sheet 12.

The sheet 10 of splint material may be stored in a folded configuration as shown in FIG. 2, thus occupying a minimum amount of space so that the material may be enclosed in a small conveniently sealed package (not shown). The sheet 10 of splint material may be manually unfolded and bent into the desired shape for use as a splint 15 by medical technicians or doctors at the scene of an injury-producing accident.

The foam-covered thin aluminum sheet material for use in fashioning splints and neck braces has the desirable general properties of being light in weight, being easily packaged in a compact oval form, being transparent to X-rays, and being useable for all sizes of patients. This makes it advantageous for use by emergency medical teams, in particular ski safety patrol teams whose equipment is limited in weight because of the mode of travel.

Ambulance crew personnel need not carry a selection of different sizes of splints since the present splint material, in folded form, takes so little room and may be formed on the scene of an accident into a splint for nearly any eventuality of broken limbs. Since the material is thin and soft it may be cut easily using scissors which are always available to emergency crew personnel, to enable such personnel to prepare a splint in the necessary size, and to form the splint to conform to the body of the injured person in the most comfortable manner possible.

Referring now also to FIGS. 4 and 5, a splint 15 for supporting an injured arm 17 and wrist is made according to the present invention by manually forming the elongate sheet of material according to the invention into a beam having a "T" cross-sectional shape. This is done by folding the splint material 10 along a centrally-located longitudinal axis 20 of the elongate sheet. Thereafter, the lateral portions 22 and 24 thus defined are folded apart in opposite directions along fold lines 26 and 28 which are substantially parallel with the axis 20 to form the arms 30 and 32 of the T shape. The base, or vertical stem portion 36, of the T thus includes two parallel layers of the sheet metal as the legs of a narrow U shape of which the central longitudinal axis 20 is the bottom. The distance between the longitudinal axis 20 and the folds 26 and 28 may vary over the length of the splint 15, but is preferably at least about 0.25 inch. The flat top of the T shape is then placed against the patient's injured limb 17. The arms 30 and 32 of the T shape should be bent upwardly, as shown most clearly in FIG. 5, to conform further to the shape of the injured limb 17 and to provide ample support for the injured limb without concentrated pressure at any location. The piece of splint material 10 may also be shaped by manually bending the soft metal sheet to conform to bony protrusions such as the patient's wrist and elbow without excessive pressure. The splint 15 is fastened to the injured limb 17 to support the fleshy portions of the arm 17 gently but firmly to prevent motion which could cause additional trauma in the case of a bone fracture within the splinted limb.

The splint formed thus in accordance with the present invention may be held in place by many conventional means, including elastic bandages, adhesive tape 33, or a wrapping secured in place by the use of mating hook-and-loop fastener materials of the type sold under the trademark Velcro.

Depending on the extent of the particular injury which has occurred, a portion of the elongate sheet 10 of splint material may be provided on each side of an injured limb, as shown in FIG. 4, where a transverse bend 34 located near the middle of the length of the elongate sheet extends around the arm of the patient near the elbow.

Alternatively, the elongate sheet 10 of material may be folded in a similar location along a transverse fold 38 (FIGS. 6 and 7), bringing the resulting two longitudinal sections of the elongate sheet of material closely parallel with one another before the splint material is bent into the T-shaped beam structure previously described. In either case, the vertical base or trunk portion 36 of the T extends outwardly from the surface of the limb 17 being supported by the splint 15, acting as a longitudinal, outwardly-extending flange or rib which stiffens the splint. This provides the structural strength required to support the injured limb despite the inability of the ribbon-like elongate sheet 10 of soft material to provide such support before being bent to include the T-shaped beam structure. In some instances it may even be desirable to provide three or more layers of the splint material 10 thus bent to conform to an injured limb and one another, in the T-shaped beam configuration described, where an unusual amount of strength is required.

As shown in FIGS. 8 and 9, the material of the invention may be used in a narrower strip for use as a finger splint 40 incorporating the T-shaped beam, including a stem 36' and arms 30' and 32'. Such a strip may be manufactured in a narrower width or a wider piece may be cut down. In the latter case, it is desirable to fold over a narrow marginal portion to hide the edge of the metal sheet 12. Such a finger splint 40 may be formed manually in a bent configuration to support a finger 42 in a desired amount of flexure. A portion 44 of the material extends around the tip of the finger 42 and is bent to conform to the back of the finger, providing protection of the tip and back of the finger against being reinjured. The finger splint 40 is particularly useful in connection with surgery on fingers, where it is desired to provide padding and protection for a finger, tailored specifically to the finger. The finger splint 40 may be fastened to the finger 42 in a conventional manner.

The splint material of the present invention is also particularly useful in the form of a cervical collar or neck brace 50, shown in FIGS. 10 and 11. For this application, the elongate sheet 10 of material is wrapped completely around the patient's neck as a collar, with the opposite ends 52 and 54 of the elongate sheet overlapping one another. The sheet 10 of material should have a width 14 about equal to the length of a person's neck, or at least about 3 inches, and preferably about 4 inches. At locations spaced apart from one another around the circumference of the patient's neck, outwardly-projecting, vertically-extending stiffening "posts" or flanges 56 are defined by sets of three substantially parallel folds which will support the patient's neck and head against lateral movement.

Each flange has a central fold 58 of about 180° which forms an area of doubled thickness and places the two portions of the splint material 10 on either side of that fold 58 substantially parallel and alongside one another. Each central fold 58 extends substantially transversely across the elongate sheet of splint material 10. The generally parallel folds 60 and 62 are located, respectively, on either side of the central fold, at a distance of 0.25-1.0 inch, for example, the two layers of the material are bent apart along folds 60 and 62, which are bent in the opposite direction from the fold 58, and include an angle of about 90 degrees each. The flange 56 stands out directly away from the patient's neck when the cervical splint or collar 50 is applied, thus including the T shape used in the splint 15. Because of the flexibility of the splint material 10, the folds 60 and 62 may not be exactly parallel and straight, but may vary somewhat in distance from the central fold 58 to provide a snug fit of the collar 50.

To provide the greatest security for the flanges, top and bottom corner portions 68 of each of the flanges 56 can be folded over to prevent the central fold 58 of each flange from opening.

The longitudinal marginal portions 64 and 66 (FIG. 1) of the splint material 10 become top and bottom edges of a collar 50 formed in this manner. Because of the flexibility of the aluminum sheet material 12, these marginal portions 64 and 66 may be flared outwardly to conform to the contours of the patient's jaw and collar-bones to provide comfortable, yet firm, support for the patient's neck. To provide comfortable padding in this application the layer of padding material 16 should be within the range of 1/32 inch to ⅛ inch in its thickness 18, with the thickness 18 preferably in the range of 1/32 inch to 5/32 inch.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A collar-like splint for supporting a person's neck, comprising:
   (a) an elongate sheet of malleable metal, said sheet extending circumferentially about the person's neck as a generally tublar collar;
   (b) said sheet having a width at least about equal to the length of the person's neck, so that said splint can rest upon the person's chest and shoulders while supporting the person's head and neck, and said sheet having a length at least sufficient to extend completely around the person's neck with at least some amount of circumferential overlap; and
   (c) at least one flange extending generally vertically and projecting radially outward from said tubular collar, each said flange comprising a pair of substantially parallel portions said metal sheet defined by a pair of oppositely-directed outward bends of about 90° and an inward bend of about 180° located between said outward bends, said bends being located along lines extends generally transversely of the length of the sheet and said inward bend being separated from each of said pair of outward bends by a distance of at least about 0.25 inch.

2. The neck splint of claim 1, including at least four of said flanges located respectively on the left and right sides, the front, and the rear of the person's neck.

3. The neck splint of claim 1 wherein said sheet of metal has a layer of a resilient foam material attached thereto by an adhesive, said layer of foam material being substantially coextensive with said sheet.

4. the splint of claim 3 wherein said foam material is a microcellular urethane foam.

5. The neck splint of claim 1, said sheet having a width of at least about 3 inches add a length of at least about 24 inches.

6. The neck splint of claim 1 wherein said malleable metal is soft aluminum and wherein said sheet is thin enough to be bent easily to the required shape by hand.

7. The neck splint of claim 6 wherein said sheet has a thickness in the range of 0.005 to 0.025 inch.

8. The neck splint of claim 1, said metal sheet including laterally opposite longitudinal edges, said edges being bent outwardly to conform with the person's head and shoulders at a top and bottom of said neck splint.

9. The neck splint of claim 1 wherein said sheet has a pair of opposite faces and a layer of padding material attached to each of said faces by an adhesive, each said layer being flexible along with said sheet and having a thickness in the range of 1/32 inch to ⅛ inch.

10. An improved splint for supporting an injured body member, comprising:
    (a) an elongate sheet of malleable metal having a length and a width, said metal being bent along substantially parallel fold lines extending longitudinally of said sheet so as to define, over at least a portion of the length of said sheet, a longitudinally extending configuration having a T-shaped cross-section, including a vertical trunk portion having a double thickness of said sheet of metal, and a pair of arms each having a single thickness of said sheet metal;
    (b) said vertical trunk portion comprising two thicknesses of said sheet of metal located side by side and substantially parallel with one another and joined with one another, defining the bottom of said vertical trunk, by said sheet of metal being bent along a fold of 180° extending longitudinally of the elongate sheet of metal;
    (c) said arms being defined by said sheet of metal being bent along respective parallel opposite folds of approximately 90° in opposite directions away from said vertical trunk member, the arms extending generally oppositely away from one another adjacent said opposite folds, and respective portions of each of said arms, located spaced apart from said opposite folds, being conformed generally to the surfaces of a limb which said splint is used to support, with the vertical trunk portion extending away from said limb as a stiffening flange, said elongate sheet of metal being thin enough to be manually bent into said configuration having a T-shaped cross-section without tools; and
    (d) said elongate sheet being bent along a transverse fold line defining two parallel longitudinal segments, the two segments being folded together into said configuration having a T-shaped cross section with corresponding portions of the two longitudinal segments lying alongside one another and being substantially in contact with each other.

11. The splint of claim 10, said sheet having a thin layer of a foam plastic material attached thereto by an adhesive over substantially its entire surface.

12. The splint of claim 11 wherein said foam plastic is an expanded ethylene acetate microfoam material.

13. The splint of claim 10 wherein said elongate sheet has a width of at least about 3½ inches and a length of at least about 20 inches.

14. The splint of claim 10 wherein said metal is soft aluminum having a thickness no greater than about 0.025 inch.

15. An improved splint for supporting an injured body member, comprising:
    (a) an elongate sheet of malleable metal having a length and a width, said metal being bent along substantially parallel fold lines extending longitudinally of said sheet so as to define, over at least a portion of the length of said sheet, a longitudinally extending configuration having a T-shaped cross-section, including a vertical trunk portion having a double thickness of said sheet of metal, and a pair of arms each having a single thickness of said sheet metal;
    (b) said vertical trunk portion comprising two thicknesses of said sheet of metal located side by side and substantially parallel with one another and joined with one another, defining the bottom of said vertical trunk, by said sheet of metal being bent along a fold of 180° extending longitudinally of the elongate sheet of metal;

(c) said arms being defined by said sheet of metal being bent along respective parallel opposite folds of approximately 90° in opposite directions away from said vertical trunk member, the arms extending generally oppositely away from one another adjacent said opposite folds, and respective portions of each of said arms, located spaced apart from said opposite folds, being conformed generally to the surfaces of a limb which said splint is used to support, with the vertical trunk portion extending away from said limb as a stiffening flange, said elongate sheet of metal being thin enough to be manually bent into said configuration having a T-shaped cross-section without tools; and (d) said elongate sheet defining two longitudinal segments, a first of said segments being bent to said configuration including said T-shaped cross section, and the other of said segments extending generally parallel with and spaced apart from the first of said longitudinal segments and being bent to conform with an opposite side of a body member supported by said first longitudinal segment.

16. The splint of claim 15, said sheet having a thin layer of a foam plastic material attached thereto by an adhesive over substantially its entire surface.

17. The splint of claim 16 wherein said foam plastic is an expanded ethylene acetate microfoam material.

18. The splint of claim 15 wherein said elongate sheet has a width of at least about 3½ inches and a length of at least about 20 inches.

19. The splint of claim 15 wherein said metal is soft aluminum having a thickness no greater than about 0.025 inch.

* * * * *

UNITED STATES PATENT AND TRADEMARK OFFICE
CERTIFICATE OF CORRECTION

PATENT NO. : 4,676,233
DATED      : June 30, 1987
INVENTOR(S): Samuel Scheinberg It is certified that error appears in the above-identified patent and that said Letters Patent is hereby corrected as shown below:

Col. 3, Line 2   Change "stiffnesa" to --stiffness--;
        Line 23  Change "easilY" to --easily--;
Col. 4, Line 18  Change "shcet" to --sheet--;
Col. 7, Line 20  Change "tublar" to --tubular--;
Col. 7, Line 31  After "portions" insert --of--;
        Line 35  Change "extends" to --extending--;
        Line 46  Change "the" to --The--;
        Line 49  Change "add" to --and--.

Signed and Sealed this

Twenty-first Day of June, 1988

Attest:

DONALD J. QUIGG

Attesting Officer

Commissioner of Patents and Trademarks